(12) United States Patent
Chen et al.

(10) Patent No.: US 8,933,697 B2
(45) Date of Patent: Jan. 13, 2015

(54) MEASUREMENT OF CHEMICAL EQUILIBRIUM RATIO USING A MAGNETIC RESONANCE SPECTROSCOPY SYSTEM

(75) Inventors: Albert Po-Fu Chen, Toronto (CA); Ralph Eugene Hurd, Menlo Park, CA (US)

(73) Assignee: General Electric Company, Schenectady, NY (US)

( * ) Notice: Subject to any disclaimer, the term of this patent is extended or adjusted under 35 U.S.C. 154(b) by 510 days.

(21) Appl. No.: 13/330,451

(22) Filed: Dec. 19, 2011

(65) Prior Publication Data

US 2013/0154637 A1    Jun. 20, 2013

(51) Int. Cl.
*G01V 3/00*    (2006.01)

(52) U.S. Cl.
USPC .......................................... 324/307; 324/309

(58) Field of Classification Search
USPC ........................... 324/307, 309, 312, 314, 300
See application file for complete search history.

(56) References Cited

U.S. PATENT DOCUMENTS

| | | | | |
|---|---|---|---|---|
| 4,769,602 | A | * | 9/1988 | Vinegar et al. ................ 324/303 |
| 5,064,638 | A | * | 11/1991 | Moore et al. .................. 324/310 |
| 7,251,519 | B2 | * | 7/2007 | Axelsson et al. ............. 600/410 |
| 2004/0005273 | A1 | | 1/2004 | Driehuys |
| 2009/0189605 | A1 | | 7/2009 | Hurd |

FOREIGN PATENT DOCUMENTS

WO    02056048 A1    7/2002

OTHER PUBLICATIONS

Search Report and Written Opinion from corresponding EP Application No. 12196481.1, dated Apr. 11, 2003.

* cited by examiner

*Primary Examiner* — Louis Arana
(74) *Attorney, Agent, or Firm* — Jean K. Testa; Fletcher Yoder, P.C.

(57) ABSTRACT

The use of selective RF excitation is discussed. A spectrally selective, large tip angle RF pulse is used to detect a weak signal from a first chemical species. A non-selective, small tip angle pulse is used in measuring a signal from a second chemical species in exchange with the first chemical species. The acquired resonance data provides maybe used to measure the ratio of the spectrally distinct species in exchange.

20 Claims, 6 Drawing Sheets

\# MEASUREMENT OF CHEMICAL EQUILIBRIUM RATIO USING A MAGNETIC RESONANCE SPECTROSCOPY SYSTEM

BACKGROUND

The present disclosure relates to the use of magnetic resonance (MR) spectroscopy for measurement of chemical properties or relative concentrations.

Magnetic resonance spectroscopy and (MRS) and magnetic resonance spectroscopic imaging (MRSI) techniques are known in the field of medical diagnosis and medical diagnostic imaging. The magnetic resonance (MR) modality subjects a subject to a uniform magnetic field subject to perturbation by one or more radiofrequency (RF) pulses. In particular, the uniform magnetic field homogenizes the spins of responsive material within the object such that the spins are effectively aligned. An excitation RF pulse may then be applied to synchronize the spins of the responsive material by directionally "tipping" the spins into a plane transverse to the uniform magnetic field. Upon removal of the excitation RF pulse, the spins realign with the uniform magnetic field and, in the process, emit a resonance signal. Differences in these resonance signals attributable to each nuclear species are detected by the imaging system provide useful information about the chemical species being analyzed using the MRS system.

In particular, when the responsive material (such as a hydrogen (H) or carbon-13 ($^{13}$C) atom) is a constituent of a molecule, the electron cloud of the molecule affects the magnetic field strength experienced by the responsive material. The variation in the effective magnetic field strength results in a small change to the precession frequency, or spin, of the responsive material. This variation in the precession frequency is manifested as a chemical shift that allows different molecules containing the responsive material to be distinguished from one another. For example, this chemical shift may allow different chemicals within the body to be identified and the concentration of such chemicals to be determined.

BRIEF DESCRIPTION OF EMBODIMENTS

The present disclosure includes embodiments for generating magnetic resonance data for two or more chemical species in equilibrium exchange. For example, in one embodiment a method for measuring a ratio of two or more spectrally distinct chemical species in exchange is provided. In accordance with this method, a spectrally selective RF excitation pulse is generated having a first tip angle of 30° or greater to selectively excite a first chemical species. Under equilibrium conditions between the first chemical species and a second chemical species, a non-selective RF excitation pulse is generated having a second tip angle of less than 30° to excite at least the second chemical species. The steps of generating the spectrally selective RF excitation pulse and generating the non-selective RF excitation pulse are repeated for a set number of iterations. A ratio of the first chemical species and the second chemical species in exchange is obtained based on the differential effect of the first tip angle and the second tip angle.

In a further embodiment, a memory structure is provided that physically encodes one or more executable routines. When executed, the routines cause acts to be performed that include: generating a spectrally selective RF excitation pulse having a first tip angle of 30° or greater to selectively excite a first chemical species; under equilibrium conditions between the first chemical species and a second chemical species, generating a non-selective RF excitation pulse having a second tip angle of less than 30° to excite at least the second chemical species; repeating the steps of generating the spectrally selective RF excitation pulse and generating the non-selective RF excitation pulse for a set number of iterations; and obtaining a ratio of the first chemical species and the second chemical species in exchange based on the differential effect of the first tip angle and the second tip angle.

In another embodiment, a magnetic resonance spectroscopy system is provided. The magnetic resonance spectroscopy system includes at least a primary field coil configured to generate a primary magnetic field within a volume, a radio frequency (RF) coil configured to generate RF pulses, and one or more control circuits for controlling operation of the primary field coil and the RF coil. The magnetic resonance spectroscopy system also includes a memory storing instructions to be executed by the one or more control circuits for implementing a pulse sequence. The pulse sequence, when executed, causes generation of a spectrally selective RF excitation pulse having a first tip angle of 30° or greater to selectively excite a first chemical species; under equilibrium conditions between the first chemical species and a second chemical species, generation of a non-selective RF excitation pulse having a second tip angle of less than 30° to excite at least the second chemical species; repetition of the acts of generating the spectrally selective RF excitation pulse and generating the non-selective RF excitation pulse for a set number of iterations.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION OF EMBODIMENTS

The embodiments described herein may be performed by a suitable magnetic resonance (MR) system, such as a magnetic resonance spectroscopy (MRS) or magnetic resonance spectroscopic imaging (MRSI) system. As discussed herein, one use made of such magnetic resonance systems is to measure the pH of a local environment (such as the cardiac environment or in a suspected tumor) within a patient (or other suitable living organism) by measuring the ratio of $^{13}$C bicarbonate/$^{13}CO_2$. By using a magnetic resonance modality, the pH information may be obtained non-invasively and in vivo.

The pH information may be of particular interest in a clinical or diagnostic context due to changes in pH being associated with many diseases or other conditions of interest.

Figure 1:
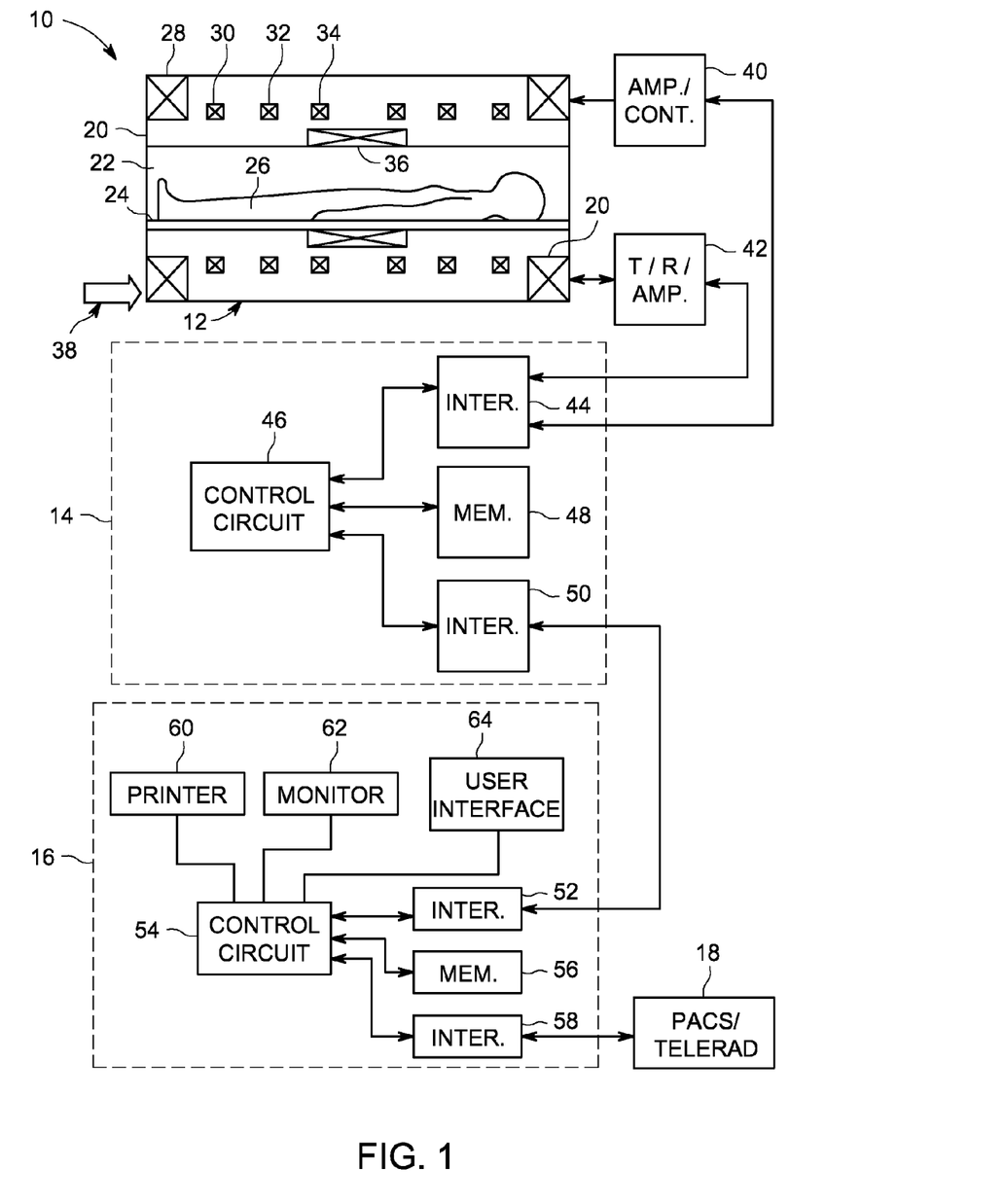
FIG. 1 is a diagrammatic illustration of an embodiment of a magnetic resonance spectroscopic imaging system configured to perform the data acquisition described herein.

With this in mind, and referring to FIG. 1, a magnetic resonance spectroscopic system 10 is illustrated schematically as including a scanner 12, a scanner control circuit 14, and a system control circuitry 16. In the depicted embodiment, the MRS system 10 is generally configured to perform spectroscopic imaging in which spatially and temporally resolved spectroscopic data is obtained. System 10 additionally includes or communicates with remote access and storage systems or devices, such as picture archiving and communication systems (PACS) 18, or other devices such as teleradiology equipment so that data acquired by the system 10 may be accessed on- or off-site. In this way, acquired data may be acquired, followed by on- or off-site processing and evaluation. While the MRS system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient. One example of a suitable system 10 is a 3T GE MR750 scanner equipped with a multinuclear spectroscopy (MNS) hardware package (both available from GE Healthcare, Waukesha, Wis.).

Scanner 12 includes a series of associated coils for producing a controlled magnetic field and for detecting emissions from one or more gyromagnetic materials within the anatomy of the subject being imaged. A primary magnet coil 28 is provided for generating a primary magnetic field generally aligned with the bore 22. In scanners 12 where acquired signals are spatially resolved (i.e., in a spectroscopic imaging system), a series of gradient coils 30, 32, and 34 are present which permit controlled magnetic gradient fields to be generated during examination sequences. A radio frequency (RF) coil 36 is provided for generating radio frequency pulses for exciting the gyromagnetic materials, such as for spin perturbation or slice selection. A separate receiving coil or the same RF coil 36 may receive magnetic resonance signals from the gyromagnetic materials during examination sequences.

The various coils of scanner 12 are controlled by external circuitry to generate the desired field and pulses, and to read emissions from the gyromagnetic materials in a controlled manner. In the illustrated embodiment, a main power supply 38 is provided for powering the primary field coil 28. Driver circuit 40 is provided for pulsing the gradient field coils 30, 32, and 34, if such gradient coils are present. Such a driver circuit 40 typically includes amplification and control circuitry for supplying current to the coils, such as in accordance with a digitized pulse sequence output by the scanner control circuit 14. Another control circuit 42 is provided for regulating operation of the RF coil 36. Control circuit 42 will typically include a switching device for alternating between the active and passive modes of operation, wherein the RF coils transmits and receives signals, respectively. Control circuit 42 also includes amplification circuitry for generating the RF pulses and for processing received magnetic resonance signals. In accordance with the present disclosure, the control circuit may operate the RF coil 36 so as to generate interleaved pulses or simultaneously generated pulses that differentially stimulate (i.e., tip) two or more different target materials.

Scanner control circuit 14 includes an interface circuit 44 which outputs signals for driving the gradient field coils 30, 32, 34 and the RF coil 36 and for receiving the data representative of the magnetic resonance signals produced in examination sequences. The interface circuit 44 is coupled to a control circuit 46. The control circuit 46 executes the commands for driving the circuit 42 and circuit 40 based on defined protocols selected via system control circuit 16. Control circuit 46 also serves to receive the magnetic resonance signals and performs subsequent processing before transmitting the data to system control circuit 16. Scanner control circuit 14 also includes one or more memory structures or circuits 48 which store configuration parameters, pulse sequence descriptions, examination results, and so forth, during operation. Interface circuit 50 is coupled to the control circuit 46 for exchanging data between scanner control circuit 14 and system control circuit 16. Such data will typically include selection of specific examination sequences to be performed (such as examination sequences or routines for generating interleaved or simultaneous RF pulses, as discussed herein), configuration parameters of these sequences, and acquired data (e.g., undersampled data) which may be transmitted in raw or processed form from scanner control circuit 14 for subsequent processing, storage, transmission and display.

System control circuit 16 includes an interface circuit 52 which receives data from the scanner control circuit 14 and transmits data and commands back to the scanner control circuit 14. The interface circuit 52 is coupled to a control circuit 54 which may include a CPU in a multi-purpose or application specific computer or workstation. Control circuit 54 is coupled to a memory structure or circuit 56 to store programming code for operation of the MRS system 10 and to store the processed image data for later reconstruction, display and transmission. For example, the programming code may execute one or more algorithms capable of performing an interleaved RF pulse signal suitable for robust pH measurement, as discussed herein. An additional interface circuit 58 may be provided for exchanging image data, configuration parameters, and so forth with external system components such as remote access and storage devices 18. Finally, the system control circuit 54 may include various peripheral devices for facilitating operator interface and for producing hard copies of the reconstructed images. In the illustrated embodiment, these peripherals include a printer 60, a monitor 62, and user interface 64 including devices such as a keyboard or a mouse.

Scanner 12 and the control circuit 46 associated therewith produce magnetic fields and radio frequency pulses in a controlled manner to excite and encode specific gyromagnetic materials within the patient 26. The scanner 12 and control circuit 46 also sense the signals emanating from such materials and perform calculations based on these signals, such as to determine a physiologically localized pH measurement based on the differential measurement of two or more target materials. It should be noted that the MRS system described herein is merely provided as one example of a suitable system, and other magnetic resonance spectroscopy system types may also be used. Similarly, such systems may be rated by the strength of their primary magnet, and any suitably rated system capable of carrying out the data acquisition and processing described below may be employed.

The MRS system 10 discussed above may perform the data acquisition techniques described herein, and, in some embodiments, the data processing techniques described herein. It should be noted that subsequent to the data acquisitions described herein, the system 10 may simply store the acquired data for later access locally and/or remotely, for example in a memory circuit (e.g., memory 56). Thus, when accessed locally and/or remotely, the acquired data may be manipulated by one or more processors contained within an application-specific or general purpose computer. The one or more processors may access the acquired data and execute routines suitable for processing or analyzing the data, as described herein.

With the foregoing discussion of a suitable system 10 in mind, the use of such a MR based spectroscopy system to calculate a localized pH measurement is discussed below. By way of example, in a physiological system, the pH of a local environment can be calculated based on the Henderson-Hasselbach equation:

$$pH = pK_a + \log\left(\frac{[HCO_3^-]}{[CO_2]}\right) \quad (1)$$

using the observed ratio of bicarbonate ($HCO_3^-$) and carbon dioxide ($CO_2$) in the environment of interest. In such a physiological environment, the ratio of $HCO_3^-$ to $CO_2$ may be established and maintained by the activity of carbonic anhydrase. Under such enzymatic equilibrium, the ratio of $[HCO_3^-]/[CO_2]$ may be on the order of approximately 15 to 20 at normal physiological pH (e.g., pH of 7.0 to 7.4), with bicarbonate being favored, at equilibrium, by greater than 10 to 1.

Certain approaches for measuring pH utilize magnetic resonance spectroscopy systems capable of measuring $^{13}C$ labeled molecules, such as measured concentrations of hyperpolarized $H^{13}CO_3^-$ and $^{13}CO_2$, at a measurement site of interest in the patient. These molecules can be derived from intravenously injected pre-polarized $H^{13}CO_3^-$ in solution or may be generated in the body from pre-polarized $[1-^{13}C]$pyruvate, which is broken down to $^{13}CO_2$ and $H^{13}CO_3^-$ through the action of pyruvate dehydrogenase. Carbonic anhydrase present in the system then establishes an equilibrium of $H^{13}CO_3^-$ and $^{13}CO_2$ based on the pH of the system.

Figure 2:
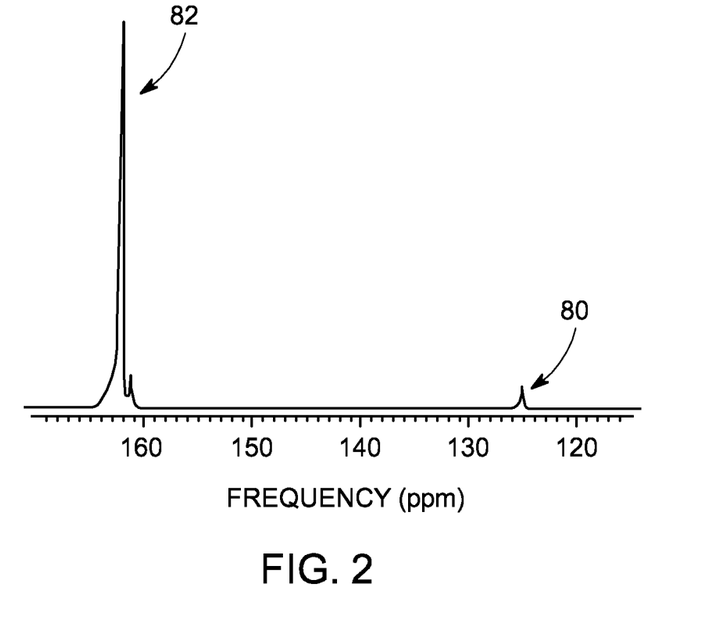
FIG. 2 depicts resonance data for $H^{13}CO_3^-$ and $^{13}CO_2$ obtained using conventional approaches.

The concentration of hyperpolarized $H^{13}CO_3^-$ and $^{13}CO_2$ may be measured at the localized site of interest using a MRS or MRSI system, such as the system 10 discussed above. Turning to FIG. 2, a set of resonance measurements are depicted where have been generated using a conventional, small tip angle RF excitation pulse (e.g., 5°) at pH 7.4 and with a ratio of $^{13}CO_3^-/^{13}CO_2$ of approximately 20. In such a measurement protocol, the measured signal attributable to $^{13}CO_2$ resonance 80 may be inadequate for robust and accurate pH measurements due to one or both of the small size of the pool of $^{13}CO_2$ undergoing measurement and the small tip angle (e.g. 5°-10° or less than 20°) of the RF excitation pulses employed to obtain temporally and spatially resolved data. In particular, a conventional small tip angle RF pulse may be non-selective and may, therefore, tip the spins of both species (e.g., $H^{13}CO_3^-$ and $^{13}CO_2$) equally. However, due to the difference in the sizes of the respective pools of $H^{13}CO_3^-$ and $^{13}CO_2$, a substantially greater signal may be observed for $H^{13}CO_3^-$ resonance 82 than for the smaller pool of $^{13}CO_2$. The potentially small signal-to-noise ratio observed for $^{13}CO_2$ in such an implementation may hinder accurate and robust measurement of pH in the local environment of interest.

With this in mind, and in accordance with the present approach, a sequence of interleaved RF excitation pulses may be employed which differentially excite (e.g., tip) the respective species undergoing measurement. For example, as depicted in the flowchart 100 of FIG. 3, a first set of RF excitation pulses 102 may be generated (block 104) which induce a small tip angle (e.g. 5°-30°) in exposed species. In one implementation discussed in this example, the first set of RF excitation pulses may be spectrally non-selective, though in other implementations the RF pulses may be spectrally selective to one or more chemical species of interest. For example, in one implementation, the non-selective RF excitation pulses 102 may each be a 200 μs hard pulse. In the pH measurement context discussed herein, the first set of pulses 102 tip the more prevalent species, $H^{13}CO_3^-$, as well as other species by the small tip angle. Resonance data readout (block 106) may be initiated after each pulse to generate resonance data 108 corresponding to the species excited by the non-selective pulse.

Figure 3:
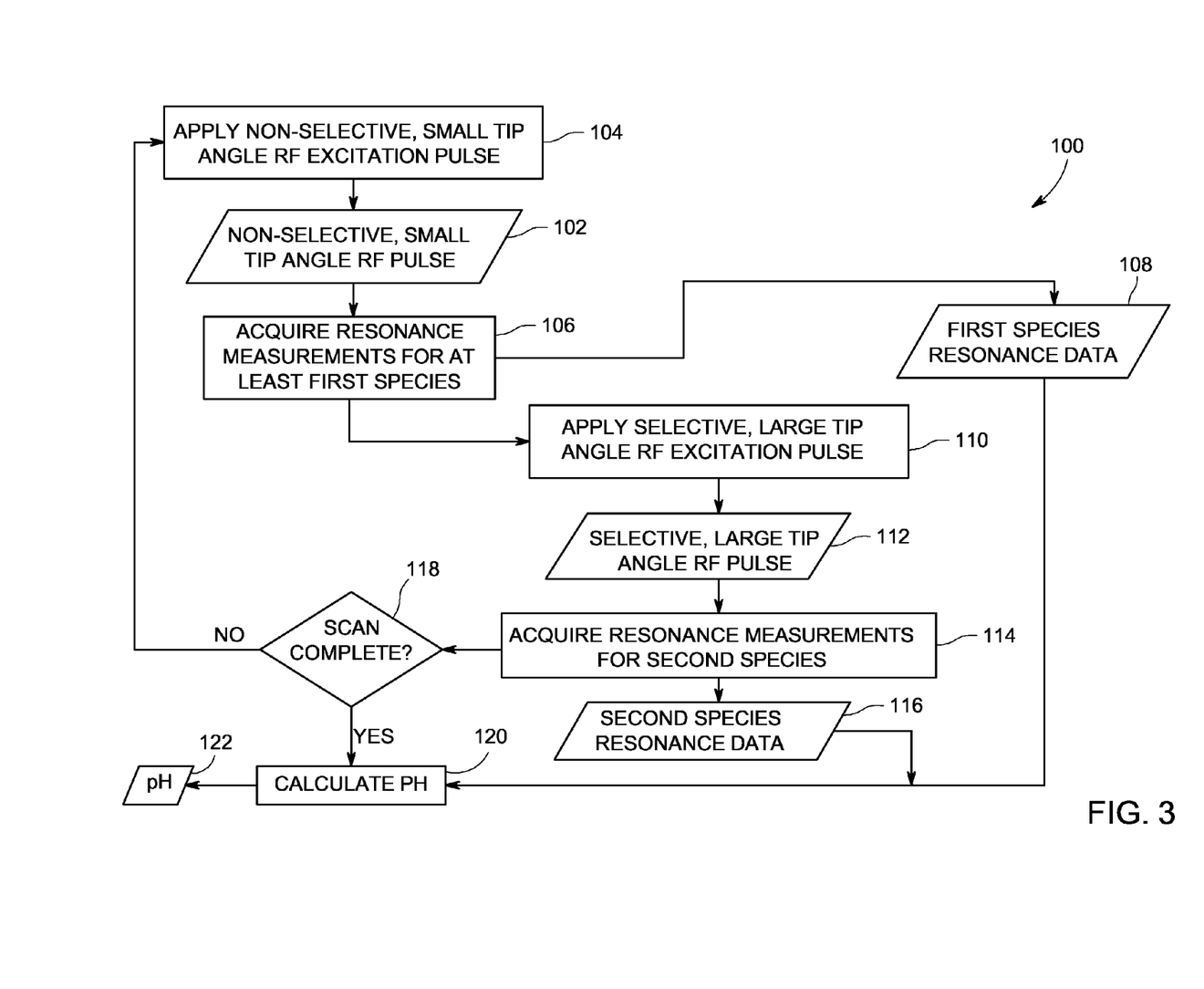
FIG. 3 depicts a flowchart of control steps or logic for application of an interleaved pulse sequence and subsequent acquisition and use of the resulting resonance data, in accordance with the present disclosure.

Between the generation of the small tip angle RF pulses 102, a second set of RF excitation pulses 112 are generated (block 110) which are spectrally selective and which induce a large tip angle (e.g. about 40° or greater) in the spectrally selected species. For example, in the pH measurement context discussed herein, the second set of pulses 112 tip $^{13}CO_2$ by the large tip angle. The resulting resonance data 116 for the spectrally selected species is acquired (block 114). In one such embodiment, the spectrally selective RF pulse 112 is a 10 ms Gaussian shaped pulse, such as a 10 ms spectrally selective RF pulse designed to have 150 Hz passband (95%) and $10^{-4}$ stopband (400 Hz from the center of the passband). In such an embodiment, the relatively large tip angle of the interleaved RF excitation pulses 112 enhance $^{13}CO_2$ sensitivity (i.e., yield a greater signal-to-noise for the $^{13}CO_2$ resonance) while the spectral selectivity of the interleaved pulses prevents saturation of the $H^{13}CO_3^-$ pool. While the preceding example describes the use of separate and discrete interleaved pulses, in other embodiments the small tip angle RF pulses 102 and the spectrally selective RF pulses 112 may be generated simultaneously using a multiband RF pulse.

With respect to an in vivo implementation directed to pH measurement, it may be appreciated that the $^{13}HCO_3^-$ and $^{13}CO_2$ pools are saturated by different amounts during the acquisition due to the tip angle difference between the interleaved RF pulses. However, in the presence of carbonic anhydrase, the $^{13}HCO_3^-$ and $^{13}CO_2$ equilibrium is restored between acquisitions of resonance data, i.e., before the next time point or k-space point is acquired. Therefore, a stable, time resolved pH measurements or an accurate pH map can still be acquired, despite this differential saturation. That is, in an equilibrium state mediated by carbonic anhydrase activity, the saturation of the magnetization of the combined $^{13}HCO_3^-$ and $^{13}CO_2$ pools by the selective $CO_2$ magnetization is small due to $^{13}CO_2$ representing less than 10% of the total $^{13}C$ pool. Thus, the signal-to-noise ratio of the $^{13}HCO_3^-$ would not be substantially affected.

Returning to FIG. 3, the interleaved generation of the of the RF pulses 102 and the spectrally-selective RF pulses 112 may proceed until the scan protocol is determined to be complete (block 118). In this manner, multiple, interleaved sets of resonance data 108, 116 for the respective first and second species of interest may be collected. The acquisition of repeated measures of the resonance data 108, 116 may allow signal averaging of the weaker signal or may allow a time resolved measure or spatial encoding of the chemical exchange ratio of the respective species to be obtained.

MRS data collected in accordance with the above approach may be subsequently processed, such as using SAGE™ software (GE Healthcare). In one in vitro implementation, the hyperpolarized $^{13}C$ phantom data may be apodized by a 5 Hz Gaussian filter in time domain prior to FFT. In one in vivo implementation, $^{13}C$ data may be apodized by a 10 Hz Gaussian filter. Peak heights may be measured from the hyperpolarized $H^{13}CO_3^-/^{13}CO_2$ phantom spectra and in vivo spectra and this resonance data may be used to calculate diagnostic parameters of interest, such as to calculate (block 120) a local pH 122 of interest within a patient.

Figure 4:
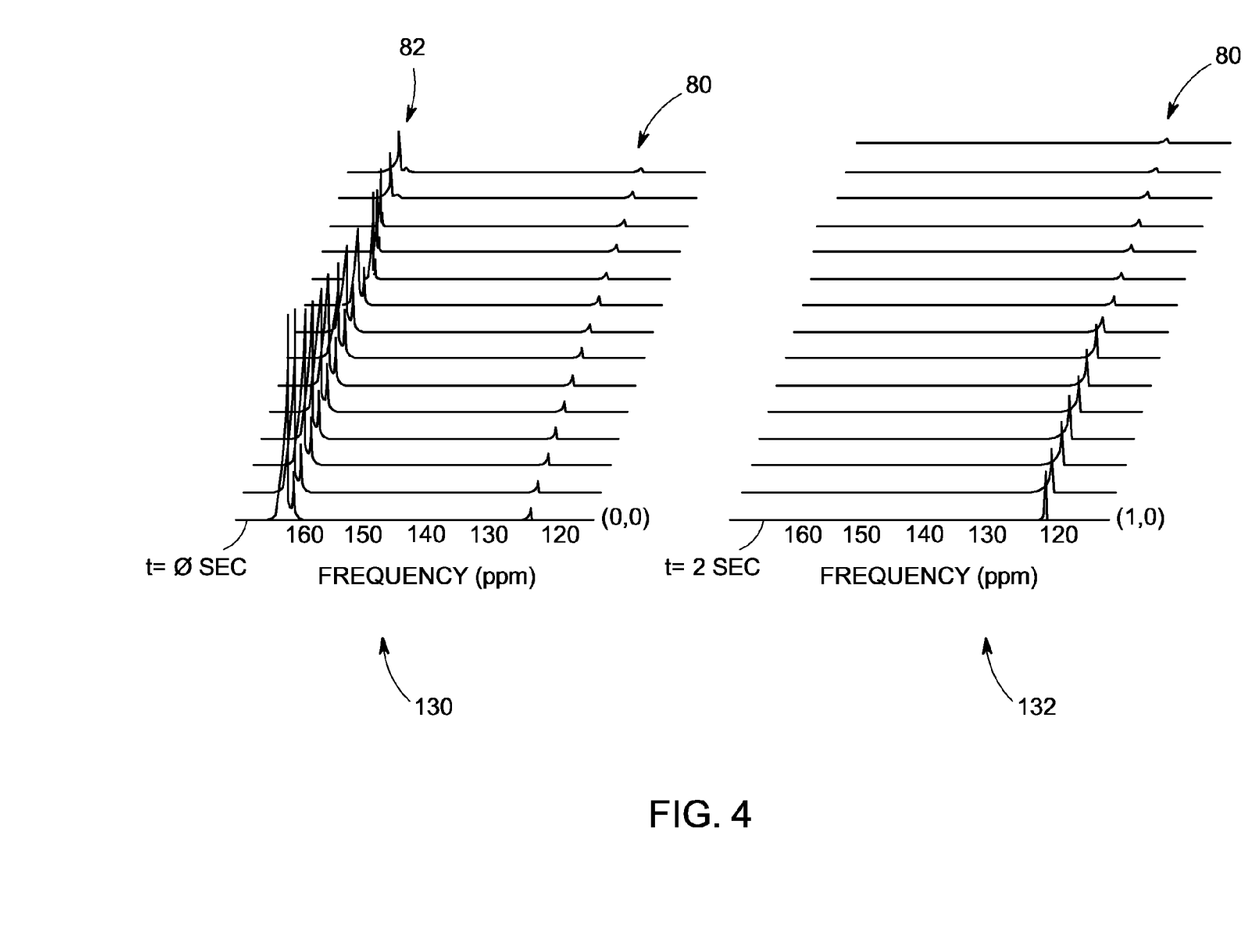
FIG. 4 depicts resonance data obtained in vitro using an interleaved set of RF pulses, in accordance with the present disclosure.
Figure 6:
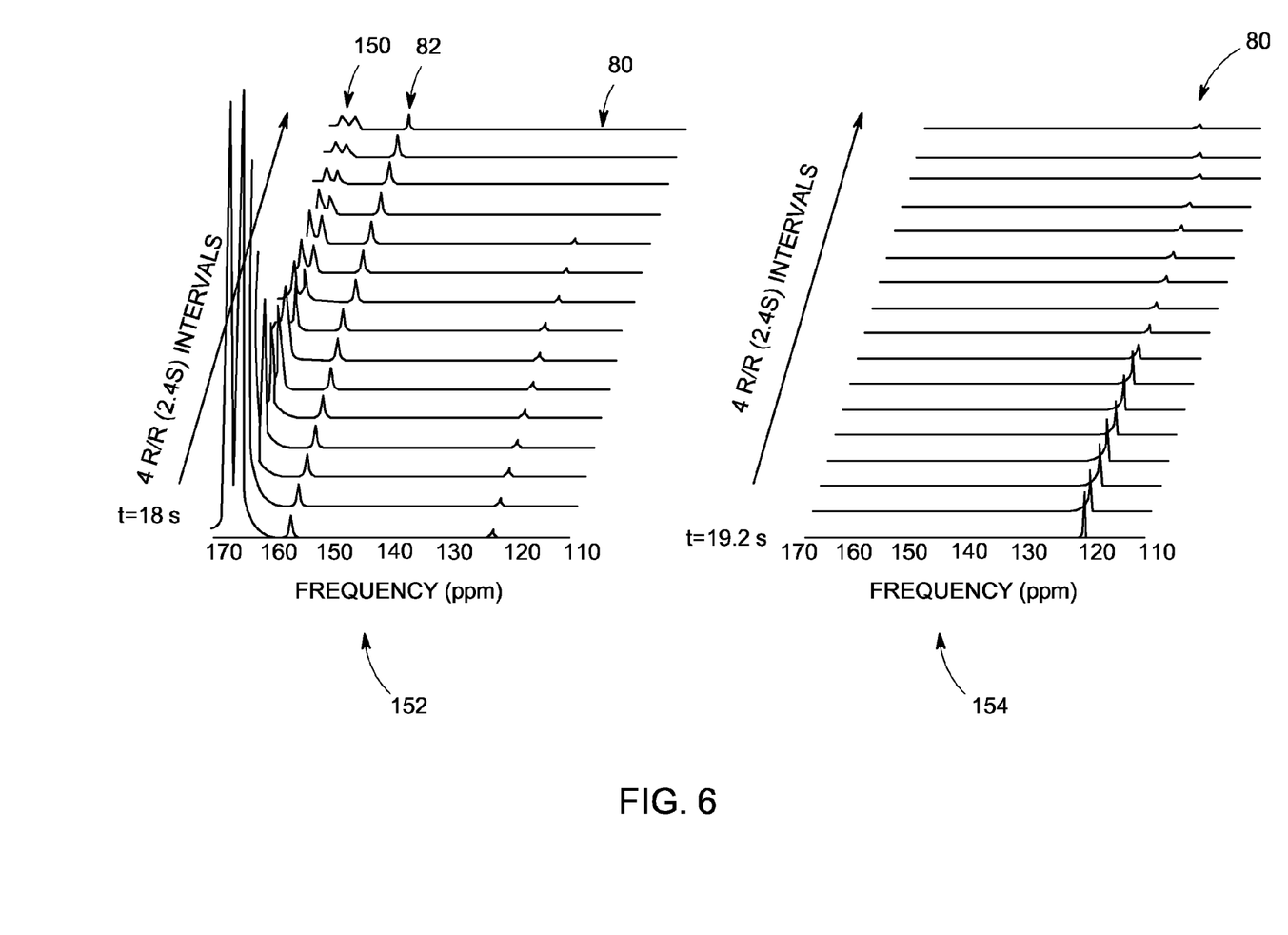
FIG. 6 depicts resonance data obtained in vivo using an interleaved set of RF pulses, in accordance with the present disclosure.

With the foregoing in mind, and turning to FIGS. 4 and 6, respective in vitro and in vivo examples of resonance data acquired in accordance with the present approach are depicted.

Example 1

In Vitro Measurement

With respect to the present in vitro and in vivo examples, all studies were performed using a 3 T GE MR750 scanner (GE Healthcare, Waukesha, Wis.) equipped with the multinuclear spectroscopy (MNS) hardware package. A micro-strip dual-tuned $^1$H-$^{13}$C volume coil with 8 cm inner diameter was used for the phantom measurements (Magvale, San Francisco, Calif.). A HyperSense DNP polarizer (Oxford Instruments, Abingdon, UK) was used to polarize the substrates at 3.35 T and 1.4 K using known polarization approaches. Sodium $^{13}$C-bicarbonate (Isotec, Miamisburg, Ohio) was prepared in glycerol with OX063 trityl radical (Oxford Instruments). Neat [1,2-$^{13}$C$_2$]pyruvic acid (Isotec) was doped with 15 mM of OX063 trityl radical (Oxford Instruments) and 1 mM Gd chelate (Prohance®, Bracco International).

For $^{13}$C-bicarbonate phantom measurements, ~30 μl of the $^{13}$C sodium bicarbonate/glycerol mixture was polarized for ~80 minutes and dissolved using 4 ml of de-ionized water/EDTA (100 mg/L). Immediately following dissolution, the $^{13}$C bicarbonate solution was mixed with 4 ml of 500 mM sodium phosphate buffer (pH 7.25) that contained 6 μg of carbonic anhydrase enzyme (Isozyme II, from bovine erythrocytes, >3,000 W-A units/mg protein, Sigma Aldridge, St. Louis, Mo.). Approximately 5 ml of this final mixture was then used in each phantom experiment.

With respect to data acquisition, a pulse-acquire pulse sequence was modified to allow toggling of the excitation RF pulses. A 10 ms spectrally selective RF pulse designed to have 150 Hz pass-band (95%) and 10$^{-4}$ stop-band (400 Hz from the center of the pass-band) was interleaved with a 200 μs hard pulse between transients. Readouts (10,000 Hz/4096 pts) started immediately after each RF pulse. Dynamic magnetic resonance spectroscopy (MRS) data were acquired using the interleaved RF pulses scheme after the pre-polarized H$^{13}$CO$_3^-$ in solution was placed inside the RF coil (n=4, TR=2 s, 96 transients). The RF transmitter was centered on the $^{13}$CO$_2$ resonance when that the selective RF pulse was used, and it was centered between H$^{13}$CO$_3^-$ and $^{13}$CO$_2$ when the hard pulse was used. Nominal tip angles for the selective pulse and the hard pulse were set to 40° and 10°, respectively. The Henderson-Hasselbalch equation was applied to estimate the pH in the solutions using a pK$_a$ value of 6.15. When $^{13}$CO$_2$ signals from the selective RF pulse were used to calculate pH, tip angle and echo time (effective echo time of 5 ms was used) corrections were performed; T$_1$ corrections were also made for H$^{13}$CO$_3^-$ signals (to account for the polarization decay of H$^{13}$CO$_3^-$ between the transient that H$^{13}$CO$_3^-$ signal was measured and the next transient that selective $^{13}$CO$_2$ signal was measured). Echo time corrections were made using T$_2$* based on linewidth of $^{13}$CO$_2$ measured in the spectra. H$^{13}$CO$_3^-$ T$_1$ was estimated from experiments in which only the hard pulse was used.

With the foregoing methodology in mind, a graphical depiction of resonance data acquired in such an in vitro implementation is depicted in FIG. 4. As depicted in FIG. 4, a first set of acquired resonance data 130 corresponds to the resonance data read out in response to the non-selective, small tip angle (e.g., 5°-30°) RF excitation pulse 102, i.e., a 200 μs hard pulse. As depicted in the sample resonance data, the first set of resonance data 130 includes resonances for H$^{13}$CO$_3^-$ (resonances 82) and a trace resonance 80 corresponding to $^{13}$CO$_2$. Interleaved with the data read out in response to the non-selective RF pulses is a second resonance data set 132 read out in response to the spectrally-selective, large tip angle (e.g., 30°-90°) RF excitation pulse 112, i.e., a 10 ms spectrally selective pulse. The second set of resonance data 132 includes resonance data 80 corresponding to $^{13}$CO$_2$, but provides a better signal-to-noise ratio for the $^{13}$CO$_2$ resonance data than is observed for the non-selective acquisition.

Figure 5:
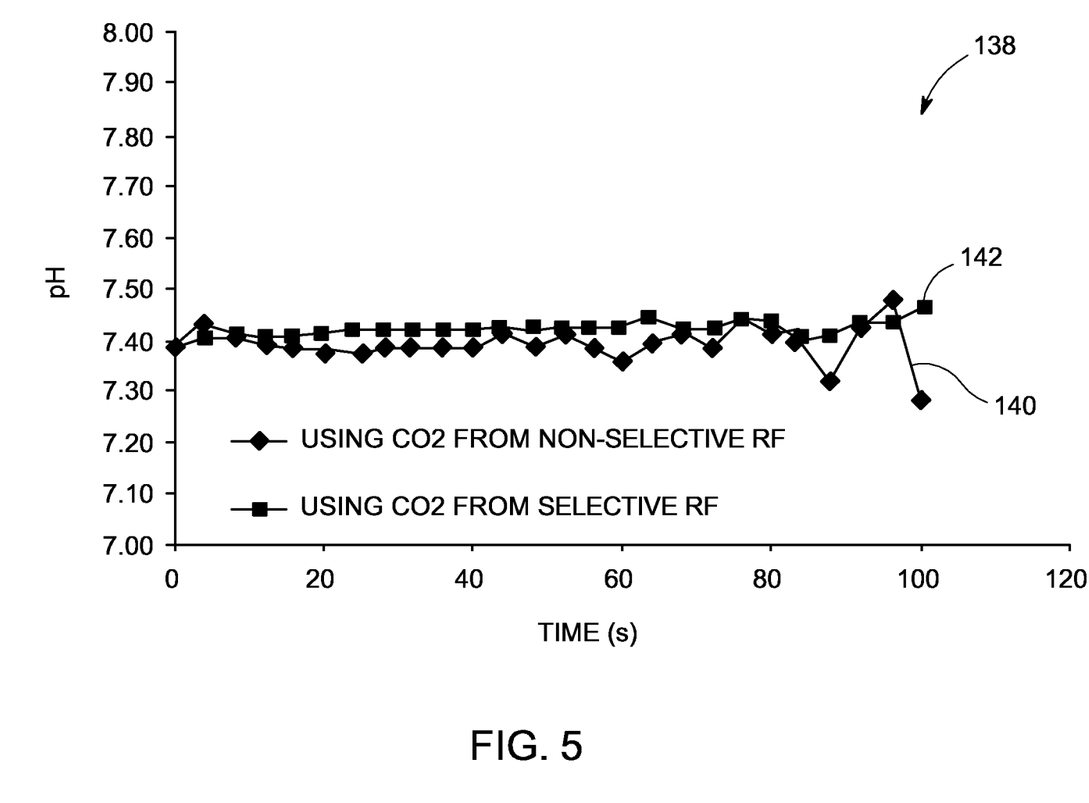
FIG. 5 depicts calculated pH based on resonance data obtained using interleaved RF pulses, in accordance with the present disclosure.

Turning to FIG. 5, a graph 138 of two separate pH measurements calculated using in vitro $^{13}$CO$_2$ measurement obtained as described above is shown. The first measurement 140 was calculated using $^{13}$CO$_2$ measurements generated using only non-selective RF pulses while the second measurement 142 was calculated using $^{13}$CO$_2$ measurements generated using $^{13}$CO$_2$-selective RF pulses. Peak resonance measurement heights were used in the calculations and tip angle (T1, T2*) corrections were performed for the data from the interleaved acquisitions. As evidenced by the graph 138, the second measurement 142 calculated using $^{13}$CO$_2$ measurements generated using $^{13}$CO$_2$-selective RF pulses is stable over time. In this example, the second measurement 142 corresponded to pH measurements in the range of 7.38 to 7.43, which generally agreed with the ph of 7.35 measured by a pH meter.

Example 2

In Vivo Measurement

In a set of in vivo measurements performed on pigs, a custom build $^{13}$C transmit/receive surface coil with $^1$H blocking and a diameter of 5" was employed. With respect to the infusate employed, 105 μl of [1,2-$^{13}$C$_2$]pyruvic acid/trityl mixture was polarized for ~60 minutes then dissolved with ~6 ml of 100 mM TRIS/250 mM NaOH solution, giving a nominal pyruvate concentration of 250 mM and pH of 7.4. This pyruvate solution was diluted with normal saline to triple the total volume and 15 ml of diluted pyruvate solution was infused into the animal in each experiment.

The $^{13}$C surface coil was placed over the chest of the pig and its positioning over the heart was confirmed by 3-plane $^1$H scout images (acquired using the body coil) that provided visualization of fiduciary markers placed on the coil. Cardiac gated, dynamic MRS data were acquired from 3 animals (~20 kg) using the same pulse sequence and interleaved RF pulse scheme used in the $^{13}$C bicarbonate phantom experiments discussed in Example 1. Data acquisition started at the same time as start of the ~15 s infusion of the 15 ml of pre-polarized [1,2-$^{13}$C$_2$]pyruvate in solution (a dose of approximately 0.06 mmol/kg). Data acquisition was cardiac gated such that one transient was performed every 2 R—R interval (one complete RF interleave cycle every 4 R—R), resulting in a TR of approximately 1-1.3 s depending on the heart rate.

With the foregoing methodology in mind, a graphical depiction of resonance data acquired in such an in vivo implementation is depicted in FIG. 6. As depicted in FIG. 6, a first set of acquired resonance data 152 corresponds to the resonance data read out in response to the non-selective, small tip angle (e.g., 10°) RF excitation pulse 102, i.e., a 200 us hard pulse. As depicted in the sample resonance data, the first set of resonance data 152 includes resonances for [1-$^{13}$C$_2$]pyruvate (resonances 150), H$^{13}$CO$_3^-$ (resonances 82), and a trace resonance 80 corresponding to $^{13}$CO$_2$. Interleaved with the data read out in response to the non-selective RF pulses is a second resonance data set 154 read out in response to the spectrally-selective, large tip angle (e.g., 40°) RF excitation pulse 112, i.e., a 10 ms spectrally selective pulses. The second set of resonance data 154 includes resonance data 80 corresponding to $^{13}CO_2$, but provides a better signal-to-noise ratio for the $^{13}CO_2$ resonance data than is observed for the non-selective acquisition.

Technical effects of the present disclosure include use of an interleaved RF pulse sequence in magnetic resonance spectroscopy where a non-selective, small tip angle RF pulse is interleaved with a spectrally selective, large tip angle RF pulse. A technical effect of the use of such an interleaved pulse sequence is the acquisition of two sets of resonance data, one of which is specific to a selected species that has a weaker signal so as to generate resonance data for that selected species having a higher signal-to-noise ratio than is observed in the resonance data generated in response to the non-selective RF pulses. A further technical effect of the present disclosure is to improve non-invasive measurement of a localized pH within a physiological environment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for measuring a ratio of two or more spectrally distinct chemical species in exchange, the method comprising the steps of:
    generating a first RF excitation pulse that selectively tips a first chemical species by a first tip angle;
    quantifying the first chemical species based on resonance signals generated in response to the first RF excitation pulse;
    under equilibrium conditions between the first chemical species and a second chemical species, generating a second RF excitation pulse that tips at least the second chemical species by a second tip angle that is different than the first tip angle;
    quantifying the second chemical species based on resonance signals generated in response to the second RF excitation pulse;
    repeating, for a set number of iterations, the steps of generating the first RF excitation pulse, quantifying the first chemical species, generating the second RF excitation pulse, and quantifying the second chemical species; and
    obtaining a ratio of the first chemical species and the second chemical species in exchange correcting for the differential effect of the first tip angle and the second tip angle.

2. The method of claim 1, wherein the steps of generating the first RF excitation pulse and generating the second RF excitation pulse are interleaved.

3. The method of claim 1, wherein the steps of generating the first RF excitation pulse and generating the second RF excitation pulse are performed simultaneously using a multiband RF pulse.

4. The method of claim 1, comprising the step of determining a pH based on the ratio.

5. The method of claim 1, wherein the step of repeating averages a resonance signal acquired for the first chemical species.

6. The method of claim 1, wherein the step of repeating provides a time resolved measure or spatial encoding of an exchange ratio between the first chemical species and the second chemical species.

7. The method of claim 1, wherein the second tip angle substantially preserves the total exchange pool of the first chemical species and the second chemical species.

8. The method of claim 1, wherein the second tip angle substantially preserves the total exchange pool of the first chemical species and the second chemical species.

9. The method of claim 1, wherein the first tip angle increases a signal-to-noise ratio for the first chemical species relative to the second tip angle.

10. A memory structure physically encoding one or more executable routines which, when executed, cause acts to be performed comprising:
    generating a first RF excitation pulse that selectively tips a first chemical species by a first tip angle;
    quantifying the first chemical species based on resonance signals generated in response to the first RF excitation pulse;
    under equilibrium conditions between the first chemical species and a second chemical species, generating a second RF excitation pulse that tips at least the second chemical species by a second tip angle that is different than the first tip angle;
    quantifying the second chemical species based on resonance signals generated in response to the second RF excitation pulse;
    repeating, for a set number of iterations, the steps of generating the first RF excitation pulse, quantifying the first chemical species, generating the second RF excitation pulse, and quantifying the second chemical species; and
    obtaining a ratio of the first chemical species and the second chemical species in exchange correcting for the differential effect of the first tip angle and the second tip angle.

11. The memory structure of claim 10, wherein the first RF excitation pulse and the second RF excitation pulse are interleaved.

12. The memory structure of claim 10, wherein the first RF excitation pulse and the second RF excitation pulse are generated simultaneously using a multiband RF pulse.

13. The memory structure of claim 10, wherein the one or more executable routines, when executed, further cause an act to be performed comprising:
    determining a pH based on the ratio.

14. The memory structure of claim 10, wherein the act of repeating averages a resonance signal acquired for the first chemical species.

15. A magnetic resonance spectroscopy system, comprising:
    a primary field coil configured to generate a primary magnetic field within a volume;
    a radio frequency (RF) coil configured to generate RF pulses;
    one or more control circuits for controlling operation of the primary field coil and the RF coil;
    a memory storing instructions to be executed by the one or more control circuits for implementing a pulse sequence, wherein the pulse sequence, when executed, causes
    generation of a first RF excitation pulse that selectively tips a first chemical species by a first tip angle, wherein the first tip angle increases a signal-to-noise ratio for the first chemical species relative to a second tip angle that is different than the first tip angle;

under equilibrium conditions between the first chemical species and a second chemical species, generation of a second RF excitation pulse that tips at least the second chemical species by the second tip angle;

repetition, for a set number of iterations, of the acts of generating the first RF excitation pulse and generating the second RF excitation pulse.

16. The magnetic resonance spectroscopy system of claim 15, wherein the RF coil is also configured to function as a receive coil that detects resonance signals generated in response to the RF pulses.

17. The magnetic resonance spectroscopy system of claim 15, comprising a separate receive coil that that detects resonance signals generated in response to the RF pulses.

18. The magnetic resonance spectroscopy system of claim 15, wherein the first RF excitation pulse and the second RF excitation pulse are interleaved.

19. The magnetic resonance spectroscopy system of claim 15, wherein the first RF excitation pulse and the second RF excitation pulse are generated simultaneously using a multiband RF pulse.

20. The magnetic resonance spectroscopy system of claim 15, wherein the memory further stores instructions to be executed by the one or more control circuits for determining a ratio of the first chemical species and the second chemical species in exchange based on the differential effect of the first tip angle and the second tip angle.

\* \* \* \* \*